United States Patent [19]

Fukui et al.

[11] Patent Number: 5,449,820
[45] Date of Patent: Sep. 12, 1995

[54] METHOD OF PREPARING HIGH PURITY 2,6-NAPHTHALENE DICARBOXYLIC ACID

[75] Inventors: Yoshio Fukui; Tatsuto Yoshioka; Chikara Sugimoto; Manabu Okuyama; Norioki Mine; Masahiko Yamagishi, all of Yokkaichi, Japan

[73] Assignee: Mitsubishi Chemical Corporation, Tokyo, Japan

[21] Appl. No.: 362,861

[22] Filed: Dec. 23, 1994

[30] Foreign Application Priority Data

Mar. 15, 1994 [JP] Japan ................................. 6-44024

[51] Int. Cl.$^6$ .............................................. C07C 5/43
[52] U.S. Cl. .................................................. 562/486
[58] Field of Search ........................ 562/486, 485, 487

[56] References Cited

U.S. PATENT DOCUMENTS

| | | | |
|---|---|---|---|
| 4,345,976 | 8/1982 | Peter | 203/49 |
| 4,514,574 | 4/1985 | Inoue et al. | 564/424 |
| 4,550,198 | 10/1985 | Myerson | 560/486 |
| 4,964,995 | 10/1990 | Chum et al. | 210/634 |

*Primary Examiner*—José G. Dees
*Assistant Examiner*—Samuel Barts
*Attorney, Agent, or Firm*—Oblon, Spivak, McClelland, Maier & Neustadt

[57] ABSTRACT

The present invention provides a method of preparing high purity 2,6-naphthalene dicarboxylic acid in which the contents of coloring substances, heavy metal and bromine compounds can be reduced by dissolving coarse crystals of 2,6-naphthalene dicarboxylic acid containing impurities in supercritical or subcritical water containing an entrainer composed of an organic solvent containing oxygen and having a specific solubility parameter, and by cooling an obtained solution to cause crystals to precipitate so as to separate the crystals from mother liquor.

5 Claims, No Drawings

METHOD OF PREPARING HIGH PURITY 2,6-NAPHTHALENE DICARBOXYLIC ACID

BACKGROUND OF THE INVENTION

1. Field of the Invention

The present invention relates to a method of preparing high purity 2,6-naphthalene dicarboxylic acid by dissolving 2,6-naphthalene dicarboxylic acid containing impurities, in particular, coarse 2,6-naphthalene dicarboxylic acid obtainable by oxidizing dialkyl naphthalene with molecular oxygen and by crystallizing the coarse 2,6-naphthalene dicarboxylic acid, the 2,6-naphthalene dicarboxylic acid being a useful compound to serve as a raw material for manufacturing resin, such as polyethylene naphthalate (PEN resin), exhibiting excellent functions.

DESCRIPTION OF THE RELATED ART

It has been known that naphthalene dicarboxylic acid can be manufactured by oxidizing, with molecular oxygen, dialkylnaphthalene, such as dimethylnaphthalene or diisopropylnaphthalene, in the presence of cobalt, manganese and bromine. However, coarse naphthalene dicarboxylic acid obtainable as a result of the foregoing method must be subjected to a refining process because it contains impurities, such as trimellitic acid, coloring substances and cobalt, manganese and bromine compounds which are generated due to the added catalyst.

Hitherto, a method of refining naphthalene dicarboxylic acid has been known which comprises the steps of dissolving coarse naphthalene dicarboxylic acid in an alkali solution; performing oxidation and hydrogenating processes and a decoloring process by means of adsorption; and by making the resulting substance to be acid, so that high purity naphthalene dicarboxylic acid is obtained (refer to Japanese Patent Laid-Open No. 48-68554, Japanese Patent Laid-Open No. 48-49747, Japanese Patent Laid-Open No. 50-105639 and Japanese Patent Laid-Open No. 50-160248). However, all of the foregoing methods use alkali and acid in large quantities, thus rising a problem in that inorganic salt and waste water in large quantities are generated.

Another method has been suggested which comprises the steps of dissolving coarse naphthalene dicarboxylic acid in an organic solvent, such as dimethyl formamide or dimethylsulfoxide; subjecting the resulting substance to activated carbon process; and performing recrystallization (refer to Japanese Patent Laid-Open No. 62-23074). However, the boiling point of the foregoing organic solvents is too high to be easily recovered. What is worse, the organic solvents have a problem of toxicity.

Another method has been disclosed which comprises the steps of dissolving coarse naphthalene dicarboxylic acid in a water solution of, such as dimethylamine; and removing the amine by distillation to precipitate naphthalene dicarboxylic acid, whereby the coarse naphthalene dicarboxylic acid is refined (refer to Japanese Patent Laid-Open No. 50-142542). However, this method suffers from a problem in that water in a large quantity is undesirably removed by distillation because amine for use in this method and water are brought into azetropy and another problem in that the recovering efficiency has been unsatisfactory because amine cannot be removed completely from the water solution.

In order to overcome the foregoing problems, a method has been suggested that uses a mixed solvent of amine and alcohol (refer to Japanese Patent Laid-Open No. 5-155807). However, the foregoing method cannot sufficiently remove impurities, such as heavy metal, generated from the catalyst.

On the other hand, a method has been suggested which is capable of removing impurities including cobalt and manganese by cleaning the impurities with water heated to 80° C. to 90° C. (see Japanese Patent Laid-Open No. 1-121237). However, also the foregoing method cannot remove impurities incorporated into coarse crystals.

As a method of refining aromatic polycarboxylic acid, a method has been known in which impurities in terephthalic acid are, in presence of a noble metal catalyst, subjected to hydrogenation in water which is in a supercritical state (see Japanese Patent Publication No. 51-38698).

A method for improving the solubility and selectivity required in the supercritical extraction has been investigated, the method having an arrangement that a third component called an "entrainer" or a "dissolving enhancing material" is added (see, for example, A. K. Sunol, et al, "ENTRAINER SELECTION IN SUPERCRITICAL EXTRACTION" on pp. 451 to 464 of Process Technology Proceedings, 3 "Supercritical Fluid Technology", edited by J. M. L. Penninger, M. Radosz, M. A. McHugn and V. J. Krukonis, published by Elsevier Science Publishers B. V., 1985.

SUMMARY OF THE INVENTION

The inventors of the present invention have intended to overcome the foregoing technological problems and, thus, an object of the present invention is to provide a method of preparing high purity 2,6-naphthalene dicarboxylic acid which is an improvement in the conventional method of preparing high purity 2,6-naphthalene dicarboxylic acid, with which the quantities of coloring substances, heavy metal and bromine compounds can be reduced, from 2,6-naphthalene dicarboxylic acid containing impurities, in particular, from 2,6-naphthalene dicarboxylic acid obtainable by oxidizing dialkylnaphthalene by using gas containing molecular oxygen in presence of heavy metal salts and bromine compounds, and in which 2,6-naphthalene dicarboxylic acid is dissolved and crystallized in subcritical water or supercritical water.

According to the present invention, there is provided a method of preparing high purity 2,6-naphthalene dicarboxylic acid characterized by dissolving coarse crystals of 2,6-naphthalene dicarboxylic acid in supercritical or subcritical water containing an entrainer selected from a group consisting of organic solvents each of which contains oxygen, and the solubility parameter of which is 18 to 35, by cooling an obtained solution to precipitate crystals, and by separating the crystals from the mother liquor.

DESCRIPTION OF THE PREFERRED EMBODIMENT

As coarse crystals of 2,6-naphthalene dicarboxylic acid containing impurities for use in the method of the present invention, 2,6-naphthalene dicarboxylic acid, the purity of which is 90% or higher, usually 95% to 99%, is employed. As an alternative to this, 2,6-naphthalene dicarboxylic acid, the purity of which is 99% or higher, for example, that previously refined with activated carbon may be used as the raw material for the process.

The coarse 2,6-naphthalene dicarboxylic acid is exemplified by coarse crystals of 2,6-naphthalene dicarboxylic acid of a type obtainable by oxidizing dialkyl naphthalene with molecular oxygen in a solvent of aliphatic lower-monocarboxylic acid or water in presence of cobalt, manganese and bromine. The coarse crystals of 2,6-naphthalene dicarboxylic acid obtainable from the oxidation reaction of dialkyl naphthalene contain cobalt, manganese and bromine compounds generated from the catalyst, 6-carboxy-2-naphthoaldehyde, trimellitic acid, brominated 2,6-naphthalene dicarboxylic acid, bromine compounds, the structure of which has been unknown, impurities and coloring substances which are by-products of the reaction. Thus, the coarse crystals of 2,6-naphthalene dicarboxylic acid usually shows a brown color. However, it may be used in the method according to the present invention as it is or the same may be cleaned with reactive solvent or the like.

The cobalt compound and the manganese compound for use in the oxidation reaction as catalysts are exemplified by: aliphatic carboxylate of cobalt and manganese of, for example, formic acid, acetic acid, propionic acid, oxalic or maleic acid; alicyclic carboxylate of the same of, for example, naphthenic acid; aromatic carboxylate of the same of, for example, benzoic acid, terephthalic acid, naphthoic acid or naphthalene dicarboxylic acid; and inorganic compound, such as acetylated substance, oxide, carbonate or halide. Among the foregoing materials, it is preferable to employ acetate or bromide. The bromine compound is exemplified by an inorganic bromine compound, such as potassium bromide, ammonium bromide, molecular bromine or hydrogen bromide; and organic bromine compound, such as methyl bromide, ethyl bromide, bromoform, ethylene bromide and brome acetate. The quantity of the bromine compound is determined such that the quantity of bromine atoms is 0.1 to 10 mol times the total mols of cobalt and manganese atoms contained in the solvent of the aliphatic carboxylic acid, and preferably 0.2 to 5 mol times.

In the method according to the present invention, it is an important fact that an organic solvent containing oxygen and having a specific solubility parameter is caused to present when the coarse 2,6-naphthalene dicarboxylic acid is dissolved in supercritical or subcritical water. By adding the entrainer, the solubility of 2,6-naphthalene dicarboxylic acid with respect to water can be further improved. Furthermore, the content of 6-carboxy-2-naphthoaldehyde can be lowered considerably. Therefore, high purity 2,6-naphthalene dicarboxylic acid can be obtained efficiently.

The solubility parameter (hereinafter sometimes abbreviate to "SP") is a parameter indicating coagulating energy of pure substances and is defined by the following equation:

$$SP = \sqrt{\frac{(\Delta H - RT)}{V_L}}$$

where H: heat of vaporization (J/mol)
$V^L$: mol volume (cc/mol)
R: gas constant
T: temperature (°K.)
(refer to "The properties of Gases and Liquids" by Robert C. Reid et al, 1977, McGraw-Hill, Inc.).

The values of solubility parameters for the various solvents can be known by referring to ALLAN F. M. Barton, "CRC Handbook of Solubility Parameters and Other Cohesion Parameters", CRC PRESS., 96, 1988 (U.S.) and the like.

The organic solvent containing oxygen that can be used in the present invention is exemplified by alcohols, ketones and ethers. In particular, it is preferable to employ the following material having the solubility parameter of 19 to 30 and exemplified by an aliphatic alcohol, such as methanol, ethanol, n-propanol, isopropyl alcohol, n-butanol, sec-butanol, i-butanol, tert-butanol, 3-pentanol, tert-amyl alcohol or cyclohexanol; an aromatic alcohol, such as benzylalcohol; and ketone, such as acetone, methylethylketone or cyclohexane. It is most preferable to employ aliphatic alcohol having 2 to 5 carbon atoms or methylethyl ketone or cyclohexanon. Materials, such as acetylacetone (SP=19.5), that can easily be dissolved at high temperatures, cannot enable the desired effect to be obtained.

The content (concentration in water) of the entrainer is usually 0.01 wt % to 40 wt %, and preferably 0.1 wt % to 20 wt %. If the content of the entrainer is too high, the entrainer is lost excessively during the operation. If the content is too low, the solubility of 2,6-naphthalene dicarboxylic acid cannot substantially be improved.

The process according to the present invention for manufacturing high purity 2,6-naphthalene dicarboxylic acid from coarse 2,6-naphthalene dicarboxylic acid is as follows:

(1) Coarse 2,6-naphthalene dicarboxylic acid in a predetermined quantity is, at a predetermined temperature, dissolved in supercritical or subcritical water containing the entrainer in a predetermined quantity. The temperature of supercritical or subcritical water is 275° C. or higher, usually 275° C. to 380° C., and preferably 300° C. to 350° C. The pressure is set to a saturated pressure required to maintain the liquid phase in a temperature region lower than the critical temperature, while the same is set to a level higher than the critical pressure in the temperature region higher than the critical temperature. It is preferable to set the pressure to be a level higher than the saturated pressure or the critical pressure by 10 kg/cm². If the temperature of water in which coarse 2,6-naphthalene dicarboxylic acid is dissolved is too low, the solubility is lowered. If the temperature of water is too high, 2,6-naphthalene dicarboxylic acid is decomposed undesirably.

Although the quantity of water for use in the dissolving process differs depending upon the dissolving temperature, the quantity of water must be larger than a quantity (the saturated solubility) in which coarse 2,6-naphthalene dicarboxylic acid can be completely dissolved. In an example case where water containing 5 wt % of isopropanol is used and the dissolving temperature is 300° C., five parts or more by weight of water with respect to one part by weight of coarse 2,6-naphthalene dicarboxylic acid is required. An example of the results of measurements of the solubility of 2,6-naphthalene dicarboxylic acid with respect to high temperature and high pressure water is shown in Table 1.

TABLE 1

Temperature Dependency of solubility of 2,6-naphthalene dicarboxylic acid

| Temperature | Pressure (atm) | Solubility (wt %) Water |
|---|---|---|
| 225 | 27 | 0.36 |
| 250 | 40 | 1.13 |
| 275 | 60 | 3.28 |
| 300 | 86 | 8.34 |
| 325 | 121 | 18.6 |
| 375 | 230 | 34.2 |
| 386 | 230 | 36.7 |

As shown in Table 1, the solubility of 2,6-naphthalene dicarboxylic acid with respect to water is raised rapidly in a high-temperature region not lower than 300° C. which is near the critical point for water. At a temperature of about 370° C., which is the critical temperature for water, 30 wt % or more 2,6-naphthalene dicarboxylic acid is dissolved. If the temperature is higher than the critical temperature for water, water under pressure higher than the critical pressure has characteristics similar to water, the temperature of which is lower than the critical temperature. Therefore, the temperature dependency of the solubility can be considered to be continuous characteristics.

The presence of the entrainer further improves the solubility of 2,6-naphthalene dicarboxylic acid such that the solubility is 4.2 wt % at 250° C. and 18.0 wt % at 300° C. in a case where 2,6-naphthalene dicarboxylic acid is dissolved in water containing 5 wt % of isopropanol. Thus, the region, in which the solubility is rapidly raised, can be lowered to a temperature region not lower than 275° C.

In usual, molecules of supercritical fluid resemble a balloon floating in air to aggregate and surround (form clusters of solute and water) solid and liquid molecules present in the interface so as to raise the same. Therefore, the raised molecules can be dispersed in the supercritical fluid. Dissolving in supercritical water is meant that the foregoing state is realized.

(2) After 2,6-naphthalene dicarboxylic acid has been dissolved, the obtained solution is, under pressure whose level is higher than the saturated pressure required to maintain the solution at a liquid phase, cooled to a temperature lower than the dissolving temperature by 5° C. or more, and preferably by 10° C. or more, that is, usually 275° C. or lower, preferably to a region from 80° C. to 270° C., and most preferably to a region from 160° C. to 250° C. Thus, crystals of 2,6-naphthalene dicarboxylic acid are precipitated. Although it is preferable to lower the temperature for the purpose of improving the efficiency of recovering 2,6-naphthalene dicarboxylic acid, it is preferable that the temperature be 80° C. or higher in order to maintain the solubility of impurities. The cooling operation may be performed by, for example, flushing a portion of the solvent or by exchange heat with respect to low-temperature water.

(3) Crystals of 2,6-naphthalene dicarboxylic acid are separated from the mother liquor in which impurities are dissolved. The separation is usually performed at the temperature not more than the temperature at which the cooling and precipitation are performed, that is, usually 275° C. or lower, specifically from 80° C. to 275° C., and preferably 160° C. to 250° C. The separation can be performed by sedimentation, centrifugal separation, filtration or a method in which the mother liquor is substituted by pure water, the pressure of which is the same as the mother liquor and the foregoing separating method is employed or evaporating the substituent water, so that water is removed.

The dissolution and crystallization processes can be performed by a continuous method or a batch method. A multistage dissolution and crystallization method may be performed in which the foregoing operation is repeated several times, if necessary.

Crystals of high purity 2,6-naphthalene dicarboxylic acid may be cleaned with water or another solvent, if necessary.

Thus, the method according to the present invention enables high purity 2,6-naphthalene dicarboxylic acid to be manufactured in which the quantity of impurities can be reduced significantly, for example, such that the content of bromine is 10 ppm or lower. The mother liquor after the separation can be used again by separating the impurities by a process, such as distillation.

A fact has been known that the solubility is usually rapidly changed in the supercritical state due to change in the temperature and pressure. Such a rapid change in the solubility of 2,6-naphthalene dicarboxylic acid has not been expected. The rapid change in the solubility of 2,6-naphthalene dicarboxylic acid in the range from temperatures not higher than the critical temperature to the critical temperature is considered that it is a singular phenomenon occurring due to a fact that the critical temperature of 2,6-naphthalene dicarboxylic acid and that of water are substantially the same.

On the other hand, coloring substances and impurities generated due to the catalyst that are contained in coarse crystals of 2,6-naphthalene dicarboxylic acid obtainable by oxidizing dialkyl naphthalene with the gas containing molecular oxygen in the presence of heavy metal salts and bromine compounds maintain sufficiently excellent solubility at temperatures from 80° C. to 275° C. Therefore, use of the considerably great singular temperature dependency of the solubility of the 2,6-naphthalene dicarboxylic acid with respect to water and that of the great solubility of supercritical water or subcritical water enable coarse 2,6-naphthalene dicarboxylic acid to be significantly easily crystallized and refined.

Since forming of clusters of solute and water described in (1) is due to the interaction between the solute and water, the forming is affected by the shape, size, polarity and solubility parameters of the molecules. The reason why the method according to the present invention enables bromine compounds, in particular, brominated naphthalene dicarboxylic acid, that cannot be satisfactorily separated by the conventional method, to be separated satisfactorily will now be considered. When the temperature is in a low region, naphthalene dicarboxylic acids interact considerably and thus clusters are formed by the naphthalene dicarboxylic acids while incorporating the brominated naphthalene dicarboxylic acids. Therefore, the separation of the brominated naphthalene dicarboxylic acid cannot be performed easily. Since forming of clusters of solute and water becomes dominant in a low density region, such as in supercritical water or subcritical water, clusters of naphthalene dicarboxylic acid and water and those of brominated naphthalene dicarboxylic acid and water are formed individually. Therefore, the separation cannot be performed. The presence of the entrainer that has affinity for both water and 2,6-naphthalene dicarboxylic acid enables clusters to be formed while causing the entrainer molecules to intervene. As a result, the solubility can be further improved. Furthermore, presence of reducing compound, e.g. alcohols causes aldehydes to be reduced. Thus, it can be expected that impurities, such as 6-carboxy-2-naphthoaldehyde, have been converted into substances that can be easily dissolved in water.

That is, the method according to the present invention requires that the dissolution temperature condition are in the supercritical or subcritical state. Therefore, it is difficult to expect that the method according to the present invention enables the bromine compounds and aldehydes, that have been difficult to be separated from each other by the conventional method, to be simultaneously and easily separated from each other.

EXAMPLES

Examples the present invention will now be described.

Reference Example 2050 g of acetic acid, 0.80 g (3.2 millimols) cobalt acetate.tetrahydric salt, 3.93 g (16.0 millimols) manganese acetate.tetrahydric salt and 0.95 g (7.98 millimols) of potassium bromide were injected into an autoclave comprising a distillation cooling unit, a gas introduction pipe, a raw-material-liquid supply pump, a back-pressure controller and an induction stirrer and made of 5L-titanium to substitute the inside of the reactive system with nitrogen. The back-pressure controller was operated to make the pressure in the system to be 25 kg/cm$^2$G. The temperature in the autoclave was raised to 200° C. Air was supplied from the liquid-phase portion at a rate of 12 NL/minute, while nitrogen was supplied from the gas-phase portion at a rate of 19 NL/minute in such a manner that the internal pressure was maintained at 25 kg/cm$^2$G. After the inside of the system had been stabilized, 600 g of a solution of 2,6-dimethylnaphthalene and acetic acid contained at a weight ratio of ½ was continuously supplied in two hours. After 2,6-dimethylnaphthalene had been supplied, air was continuously supplied for one hour while maintaining the inside of the system at 200° C. and 25 kg/cm$^2$G. After reactions had been completed, the autoclave was cooled to room temperature, and precipitated solid material was filtered and recovered, the solid material being then cleaned with 600 g of hot water and 600 g of methanol. The solid material was dried so that 255 g of light yellow solid body was obtained. The yield of coarse 2,6-naphthalene dicarboxylic acid was 92% and the purity measured by liquid chromatography was 97.7%.

EXAMPLE 1

25 g of coarse crystals of 2,6-naphthalene dicarboxylic acid obtained in the reference example and 5 wt % methanol solution (SP=29.7) were injected into a 300 cc autoclave made of stainless steel placed in a 300° C.-temperature-controlled bath until the autoclave was fully filled (about 160 g). The foregoing state was maintained for 1.5 hours at 350° C. and 170 kg/cm$^2$G so that the coarse crystals were dissolved in the methanol solution.

Then, the temperature in the temperature-controlled bath was lowered to 250° C. in about 3 hours so that crystals of 2,6-naphthalene dicarboxylic acid were precipitated. Then, while operating a back pressure valve to maintain the same pressure, pure water, the temperature of which was 250° C., was supplied into the autoclave at a rate of 2.0 ml/minute for four hours by a pump. Thus, the liquid phase in the autoclave was substituted with pure water, the temperature and the pressure of which were the same as those of the liquid phase. Then, the temperature and pressure were returned to normal temperature and normal pressure, and crystals in the autoclave were filtered and dried so that 13.5 g of crystals of high purity 2,6-naphthalene dicarboxylic acid was obtained. Results of analysis of the obtained crystals are, together with the values of coarse crystals, shown in Table 2.

The analysis of 6-carboxy-2-naphtoaldehyde was performed by the liquid chromatography, those of cobalt and manganese were performed by inductively coupled plasma, and that of bromine was performed by fluorescent X-ray (dry carbonization and extraction were performed to analyze bromine as AgBr).

The hue was evaluated by using results of absorbance at 400 nm and 500 nm obtained by dissolving 1 g of a sample in 10 ml of 25% methylamine solution and by using a 10 mm crystal cell.

EXAMPLE 2

25 g of coarse crystals of 2,6-naphthalene dicarboxylic acid obtained in the reference example and 5 wt % isopropanol solution (SP=23.4) were injected into a 300 cc autoclave made of stainless steel placed in a 350° C.-temperature-controlled bath until the autoclave was fully filled (about 160 g). The foregoing state was maintained for 1.5 hours at 350° C. and 170 kg/cm$^2$G so that the coarse crystals were dissolved in the isopropanol solution.

Then, the temperature in the temperature-controlled bath was lowered to 250° C. in about 3 hours so that crystals of 2,6-naphthalene dicarboxylic acid were precipitated. Then, while operating a back pressure valve to maintain the same pressure, pure water, the temperature of which was 250° C., was supplied into the autoclave at a rate of 2.0 ml/minute for four hours by a pump. Thus, the liquid phase in the autoclave was substituted with pure water, the temperature and the pressure of which were the same as those of the liquid phase. Then, the temperature and pressure were returned to normal temperature and normal pressure, and crystals in the autoclave were filtered and dried so that 12.7 g of crystals of high purity 2,6-naphthalene dicarboxylic acid was obtained. Results of analysis of the obtained crystals are, together with the values of coarse crystals, shown in Table 2.

EXAMPLE 3

25 g of coarse crystals of 2,6-naphthalene dicarboxylic acid obtained in the reference example and 5 wt % tert butanol solution (SP=19.6) were injected into a 300 cc autoclave made of stainless steel placed in a 350° C.-temperature-controlled bath until the autoclave was fully filled (about 160 g). The foregoing state was maintained for 1.5 hours at 350° C. and 170 kg/cm$^2$G so that the coarse crystals were dissolved in the tert butanol solution.

Then, the temperature in the temperature-controlled bath was lowered to 250° C. in about 3 hours so that crystals of 2,6-naphthalene dicarboxylic acid were precipitated. Then, while operating a back pressure valve to maintain the same pressure, pure water, the temperature of which was 250° C., was supplied into the autoclave at a rate of 2.0 ml/minute for four hours by a pump. Thus, the liquid phase in the autoclave was substituted with pure water, the temperature and the pressure of which were the same as those of the liquid phase. Then, the temperature and pressure were returned to normal temperature and normal pressure, and crystals in the autoclave were filtered and dried so that 13.4 g of crystals of high purity 2,6-naphthalene dicarboxylic acid was obtained. Results of analysis of the obtained crystals are, together with the values of coarse crystals, shown in Table 2.

EXAMPLE 4

25 g of coarse crystals of 2,6-naphthalene dicarboxylic acid obtained in the reference example and a solution containing 5 wt % of isopropanol and 0.02 wt % of toluene (SP=18.3) were injected into a 300 cc autoclave made of stainless steel placed in a 350° C.-temperature-controlled bath until the autoclave was fully filled (about 160 g). The foregoing state was maintained for 1.5 hours at 350° C. and 170 kg/cm$^2$G so that the coarse crystals were dissolved in the isopropanol solution.

Then, the temperature in the temperature-controlled bath was lowered to 250° C. in about 3 hours so that crystals of 2,6-naphthalene dicarboxylic acid were precipitated. Then, while operating a back pressure valve to maintain the same pressure, pure water, the temperature of which was 250° C., was supplied into the autoclave at a rate of 2.0 ml/minute for 4.5 hours by a pump. Thus, the liquid phase in the autoclave was substituted with pure water, the temperature and the pressure of which were the same as those of the liquid phase. Then, the temperature and pressure were returned to normal temperature and normal pressure, and crystals in the autoclave were filtered and dried so that 12.9 of crystals of high purity 2,6-naphthalene dicarboxylic acid was obtained. Results of analysis of the obtained crystals are, together with the values of coarse crystals, shown in Table 2.

EXAMPLE FOR REFERENCE 25 g of coarse crystals of 2,6-naphthalene dicarboxylic acid obtained in the reference example and water were injected into a 300 cc autoclave made of stainless steel placed in a 350° C.-temperature-controlled bath until the autoclave was fully filled (about 160 g). The foregoing state was maintained for 1.5 hours at 350° C. and 170 kg/cm$^2$G so that the coarse crystals were dissolved in the isopropanol solution.

Then, the temperature in the temperature-controlled bath was lowered to 250° C. in about 3 hours so that crystals of 2,6-naphthalene dicarboxylic acid were precipitated. Then, while operating a back pressure valve to maintain the same pressure, pure water, the temperature of which was 250° C., was supplied into the autoclave at a rate of 2.0 ml/minute for four hours by a pump. Thus, the liquid phase in the autoclave was substituted with pure water, the temperature and the pressure of which were the same as those of the liquid phase. Then, the temperature and pressure were returned to normal temperature and normal pressure, and crystals in the autoclave were filtered and dried so that 13.4 g of crystals of high purity 2,6-naphthalene dicarboxylic acid was obtained. Results of analysis of the obtained crystals are, together with the values of coarse crystals, shown in Table 2.

TABLE 2

|  | Crude crystal | Example 1 | Example 2 | Example 3 | Example 4 | Reference Example |
|---|---|---|---|---|---|---|
| 6-carboxy-2-naphthaldehyde cotent (ppm) | 2437 | 437 | 83 | 47 | 39 | 528 |
| Co content (ppm) | 6.0 | <0.1 | <0.1 | <0.1 | <0.1 | <0.1 |
| Mn content (ppm) | 72 | <0.1 | <0.1 | <0.1 | <0.1 | <0.1 |
| Br content (ppm) | 290 | <10 | <10 | <10 | <10 | <10 |
| Absorbance (400 nm) | 1.467 | 0.273 | 0.178 | 0.200 | 0.187 | 0.347 |
| Absorbance (500 nm) | 0.352 | 0.075 | 0.026 | 0.029 | 0.024 | 0.082 |

EXAMPLE 5

A similar process to that according to Example 2 was performed except that a solution containing 5 wt % of an organic solvent shown in Table 3 was used (about 160 g) in place of the isopropanol solution in Example 2 and a coarse 2,6-naphthalene dicarboxylic acid having the content of 6-carboxy-2-naphthaldehyde shown in Table 3 was used so that high purity 2,6-naphthalene dicarboxylic acid was obtained. The quantity (g) of obtained crystals and the content (ppm) and reduction rate (%) of 6-carboxy-2-naphthoaldehyde are shown in Table 3 (the reduction rate can be calculated by the following equation). Note that in any of the foregoing case, each of contents of Co and that of Mn was 0.1 ppm or lower and that of Br was 10 ppm or lower.

Reduction Ratio of Aldehyde:
(Content of aldehyde in coarse crystals (ppm) - content of aldehyde in product (ppm)) / (Content of aldehyde in coarse crystals (ppm)) × 100

COMPARATIVE EXAMPLE

A similar process to that according to Example 2 was performed except that a solution containing 5 wt % of an organic solvent shown in Table 4 was injected until the autoclave was fully filled in place of the isopropanol solution (about 160 g) for use in Example 2 so that high purity 2,6-naphthalene dicarboxylic acid was obtained. The quantity (g) of obtained crystals and the content (ppm) and reduction rate (%) of 6-carboxy-2-naphthoaldehyde are shown in Table 4. Note that in any of the foregoing case, each of contents of Co and that of Mn was 0.1 ppm or lower and that of Br was 10 ppm or lower.

According to the present invention, high purity 2,6-naphthalene dicarboxylic acid can be easily prepared by a simple process.

TABLE 3

| Entrainer | SP | Resultant crystal (g) | NA content (ppm) in crude crystal | NA content (ppm) in resultant crystal | NA reduction rate (%) |
|---|---|---|---|---|---|
| ethanol | 26.1 | 14.7 | 975 | 96 | 90.15 |

TABLE 3-continued

| Entrainer | SP | Resultant crystal (g) | NA content (ppm) in crude crystal | NA content (ppm) in resultant crystal | NA reduction rate (%) |
|---|---|---|---|---|---|
| n-propanol | 24.8 | 13.2 | 927 | 100 | 89.21 |
| n-butanol | 28.7 | 15.7 | 975 | 84 | 91.38 |
| sec-butanol | 22.7 | 14.7 | 975 | 39 | 96.00 |
| iso-butanol | 23.0 | 14.7 | 843 | 34 | 95.97 |
| 3-pentanol | 22.2 | 13.3 | 843 | 65 | 92.29 |
| tert-amyl alcohol | 21.1 | 13.9 | 843 | 40 | 95.26 |
| cyclohexanol | 22.3 | 9.1 | 927 | 21 | 97.73 |
| benzyl alcohol | 24.6 | 15.4 | 927 | 132 | 85.76 |
| acetone | 19.7 | 15.0 | 975 | 133 | 86.36 |
| ethyl ethyl ketone | 19.3 | 14.0 | 843 | 80 | 90.51 |
| cyclohexanone | 21.3 | 12.4 | 927 | 6 | 99.35 |
| tetrahydrofuran | 18.5 | 14.6 | 975 | 350 | 64.10 |

TABLE 4

| Entrainer | SP | Resultant crystal (g) | NA content (ppm) in crude crystal | NA content (ppm) in resultant crystal | NA reduction rate (%) |
|---|---|---|---|---|---|
| toluene | 18.4 | 13.6 | 975 | 712 | 26.97 |
| propargyl alcohol | 54.1 | 16.9 | 843 | 510 | 39.50 |

Note:
SP: Solubility Parameter
NA: 6-carboxy-2-naphthaldehyde

What is claimed is:

1. A method of preparing high purity 2,6-naphthalene dicarboxylic acid comprising the steps of:
   dissolving coarse crystals of 2,6-naphthalene dicarboxylic acid containing impurities in supercritical or subcritical water containing an entrainer selected from a group consisting of organic solvents containing oxygen, said organic solvents respectively having solubility parameters from 18 to 35;
   cooling an obtained solution to cause crystals to precipitate; and
   separating said crystals from mother liquor.

2. A method of preparing high purity 2,6-naphthalene dicarboxylic acid according to claim 1 wherein temperature at which said crystals are separated from said mother liquor is 80° C. to 270° C.

3. A method of preparing high purity 2,6-naphthalene dicarboxylic acid according to claim 1 wherein temperature at which said coarse crystals are dissolved in water is 275° C. to 380° C.

4. A method of preparing high purity 2,6-naphthalene dicarboxylic acid according to claim 1 wherein said organic solvent is selected from a group consisting of alcohols, ketones and ethers.

5. A method of preparing high purity 2,6-naphthalene dicarboxylic acid according to claim 1 wherein content of said entrainer is 0.01 wt % to 40 wt %.

* * * * *